(12) United States Patent
Outtrup et al.

(10) Patent No.: US 7,078,213 B1
(45) Date of Patent: Jul. 18, 2006

(54) **ALKALINE *BACILLUS* AMYLASE**

(75) Inventors: Helle Outtrup, Ballerup (DK); Bjarne Rønfeldt Nielsen, Virum (DK); Lisbeth Hedegaard, Skodsborg (DK); Jens Toenne Andersen, Naerum (DK)

(73) Assignee: Novozymes A/S, Bagsvaerd (DK)

( * ) Notice: Subject to any disclaimer, the term of this patent is extended or adjusted under 35 U.S.C. 154(b) by 532 days.

(21) Appl. No.: 09/382,096

(22) Filed: Aug. 24, 1999

Related U.S. Application Data

(63) Continuation-in-part of application No. 09/249,558, filed on Feb. 12, 1999, now abandoned.

(60) Provisional application No. 60/146,297, filed on Feb. 27, 1998.

(30) Foreign Application Priority Data

Jan. 18, 1998 (DK) .................................... 0228/98

(51) Int. Cl.
*C12N 9/28* (2006.01)
*C11D 3/386* (2006.01)

(52) U.S. Cl. ...................... 435/202; 510/392
(58) Field of Classification Search ................ 435/202; 510/792
See application file for complete search history.

(56) References Cited

U.S. PATENT DOCUMENTS

| 4,022,666 A | * | 5/1977 | Mitsugi et al. | ................ | 195/62 |
| 4,061,541 A | * | 12/1977 | Boyer et al. | ................ | 195/66 R |
| 5,147,796 A | | 9/1992 | Ara et al. | ................... | 435/211 |

FOREIGN PATENT DOCUMENTS

| DE | 2044513 | 4/1971 |
| WO | WO 95/26397 | 10/1995 |
| WO | WO 96/23873 | 8/1996 |
| WO | WO 97/00324 | 1/1997 |
| WO | 98/05748 | 2/1998 |

OTHER PUBLICATIONS

Boyer. E.W., et al. (1972) J. Bacteriol. 110(3), 992-1000.*
Abstract, Dialog Accession No. 7114677, Biosis Accession No. 88037422, (1998).
Medda et al., "New Strains of *Bacillus* Licheniformis and *Bacillus* Coagulans Producing Thermostable a-Amylase Active at Alkaline pH", Journal of Applied Bacteriology 1980, 48, pp. 47-58.
J.E. Baker, "Interaction of Partially-Purified Amylases From Larval Anagasta Kuehniella (Lepidoptera: Pyralidae) With Amylase Inhibitors From Wheat", Comp. Biochem, Physiol., vol. 93B, No. 2, 1989, pp. 239-246.
Hayashi et al., "Properties of New Alkaline Maltohexaose-Forming Amylases", Appl. Microbiol Biotechnol (1988) 28: pp. 281-285.
Tigue et al., Production Studies on the Alkaline Amylases of Three Alkalophilic *Bacillus* SPP., Biotechnology Letters, vol. 16, No. 6 (Jun. 1994) pp. 569-574.
Xinyu et al., "Studies on Alkaline Amylase From Alkalophilic Bacterium", Institute of Microbiology, Academia Sinica, Beijing) 31 (5): 1991, pp. 364-370.
Bae et al., Kor. J. Appl. Microbiol. Bioeng., vol. 17, No. 2, pp. 160-164 (1989).
Takagi et al., Journal of Fermentation and BioEngineering, vol. 81, pp. 557-559 (1996).
Kim et al., Applied and Environmental Microbiology, vol. 61, pp. 3105-3112 (1995).
Abstract of Japanese Patent No. JP9206073 A, 1996.

* cited by examiner

*Primary Examiner*—Charles L. Patterson, Jr.
(74) *Attorney, Agent, or Firm*—Elias Lambiris; Jason Garbell

(57) ABSTRACT

The present invention relates to amylases having improved washing performance in an alkaline detergent solution at low temperature. More specifically, the present invention provides novel α-amylases from *Bacillus* sp. with improved performance in alkaline solutions, especially in alkaline detergent solutions at pH around 9–11.

12 Claims, 6 Drawing Sheets

SEQUENCE LISTING

<160> NUMBER OF SEQ ID NOS: 4

<210> SEQ ID NO 1
<211> LENGTH: 1646
<212> TYPE: DNA
<213> ORGANISM: Bacillus sp.
<220> FEATURE:
<221> NAME/KEY: CDS
<222> LOCATION: (1)...(1646)
<221> NAME/KEY: sig_peptide
<222> LOCATION: (1)...(93)
<221> NAME/KEY: mat_peptide
<222> LOCATION: (94)...(1646)

<400> SEQUENCE: 1

```
atg caa aac aca gcg aaa aac tcc atc tgg cag agg gtg cgc cac agc      48
Met Gln Asn Thr Ala Lys Asn Ser Ile Trp Gln Arg Val Arg His Ser
    -30                 -25                 -20 gcc att gcc tta tcc gct ctc agt tta tcc ttt ggc ctg cag gcc agc      96
Ala Ile Ala Leu Ser Ala Leu Ser Leu Ser Phe Gly Leu Gln Ala Ser
-15                 -10                  -5                   1 gag tta cca caa att cca cca cag cag gtg aac aac acc atg tac cag     144
Glu Leu Pro Gln Ile Pro Pro Gln Gln Val Asn Asn Thr Met Tyr Gln
                 5                  10                  15 gca ttt tat tgg gat gcc tac cct ggc ctt tgg gcc aat tta ccg gcc     192
Ala Phe Tyr Trp Asp Ala Tyr Pro Gly Leu Trp Ala Asn Leu Pro Ala
             20                  25                  30
```

-continued

| | |
|---|---|
| atg gcg gcc cct ttg gcc gag cgt ggc att acc tcg atg tgg ttg ccg<br>Met Ala Ala Pro Leu Ala Glu Arg Gly Ile Thr Ser Met Trp Leu Pro<br>35                    40                    45 | 240 |
| ccc gcc gcc aaa ggc atg aat ggt act ttc agt gtc ggt tac gat gta<br>Pro Ala Ala Lys Gly Met Asn Gly Thr Phe Ser Val Gly Tyr Asp Val<br>50                    55                    60                    65 | 288 |
| tac gat ttc tgg gat ctg ggc gag ttt aac caa aaa ggc acc acc gcc<br>Tyr Asp Phe Trp Asp Leu Gly Glu Phe Asn Gln Lys Gly Thr Thr Ala<br>              70                    75                    80 | 336 |
| acc cgt tac ggt act cgt cag cag ctg caa caa gca ctg agt gct ctg<br>Thr Arg Tyr Gly Thr Arg Gln Gln Leu Gln Gln Ala Leu Ser Ala Leu<br>                    85                    90                    95 | 384 |
| gac caa ctg ggt att cag gcc tat ttt gat gtg gtg ttt aac cac cgc<br>Asp Gln Leu Gly Ile Gln Ala Tyr Phe Asp Val Val Phe Asn His Arg<br>100                    105                    110 | 432 |
| atg ggc gcc gat gca cag gag aat att cct ggc ttt ggc ctg gcc tgg<br>Met Gly Ala Asp Ala Gln Glu Asn Ile Pro Gly Phe Gly Leu Ala Trp<br>115                    120                    125 | 480 |
| acc gag tat cat ctg caa ggt cgt cag gcg cat tat acc cag caa aac<br>Thr Glu Tyr His Leu Gln Gly Arg Gln Ala His Tyr Thr Gln Gln Asn<br>130                    135                    140                    145 | 528 |
| tgg ggc tac ttg tgg cac gac ttt gac tgg aac tgg acc gcg ttt aat<br>Trp Gly Tyr Leu Trp His Asp Phe Asp Trp Asn Trp Thr Ala Phe Asn<br>                    150                    155                    160 | 576 |
| ggc tcc gac aat cag ctc tac ccc ggc aaa tgg tgg ggc aat acc ttc<br>Gly Ser Asp Asn Gln Leu Tyr Pro Gly Lys Trp Trp Gly Asn Thr Phe<br>                    165                    170                    175 | 624 |
| cac ttc cct tat ttg atg ggt gag gat gtc gat tac aac cgc ttt gaa<br>His Phe Pro Tyr Leu Met Gly Glu Asp Val Asp Tyr Asn Arg Phe Glu<br>                    180                    185                    190 | 672 |
| gtg cag cag gaa atg aaa gcc tgg ggc gag tgg atc atc aac agc gtt<br>Val Gln Gln Glu Met Lys Ala Trp Gly Glu Trp Ile Ile Asn Ser Val<br>195                    200                    205 | 720 |
| ggc ttt agc ggc ttt cgg atg gat gcc atc gcc cat gtc gat acc gat<br>Gly Phe Ser Gly Phe Arg Met Asp Ala Ile Ala His Val Asp Thr Asp<br>210                    215                    220                    225 | 768 |
| ttt acc cgt gac tgg atc aat cac gtg cag tgg gcc acc agt gag gat<br>Phe Thr Arg Asp Trp Ile Asn His Val Gln Trp Ala Thr Ser Glu Asp<br>                    230                    235                    240 | 816 |
| gtg ttc ttt gtc gct gaa gcc tgg gtc agt gat atc aac ggc tat ctg<br>Val Phe Phe Val Ala Glu Ala Trp Val Ser Asp Ile Asn Gly Tyr Leu<br>                    245                    250                    255 | 864 |
| gat gca gtc aat acg ccg cat ttg cgc gct ttt gat ttc aat ttg cgc<br>Asp Ala Val Asn Thr Pro His Leu Arg Ala Phe Asp Phe Asn Leu Arg<br>260                    265                    270 | 912 |
| gaa gac ttc gtt gct tta agc agc ggt agc aaa gac atg cgt tgg tgg<br>Glu Asp Phe Val Ala Leu Ser Ser Gly Ser Lys Asp Met Arg Trp Trp<br>275                    280                    285 | 960 |
| ggc ggt ctg gtc aat agc cag cac cgt gat cgg gcg gtc act ttt gtc<br>Gly Gly Leu Val Asn Ser Gln His Arg Asp Arg Ala Val Thr Phe Val<br>290                    295                    300                    305 | 1008 |
| gat aac cac gat acc agc cgg gcc ggc aac cct tat ggc atg ccg cag<br>Asp Asn His Asp Thr Ser Arg Ala Gly Asn Pro Tyr Gly Met Pro Gln<br>                    310                    315                    320 | 1056 |
| gtg atc aac tac aag aac cag gcc tac gct tac att ctg ttg cgt gag<br>Val Ile Asn Tyr Lys Asn Gln Ala Tyr Ala Tyr Ile Leu Leu Arg Glu<br>                    325                    330                    335 | 1104 |
| cat ggg gtg ccg act gtg ttt gcc cgc gat tac gac gaa ttt ggc atg<br>His Gly Val Pro Thr Val Phe Ala Arg Asp Tyr Asp Glu Phe Gly Met | 1152 |

```
                340             345             350
gcg cca acg ctg gat aaa ttg att gag gcg cgc cgc tac ttt gct tat    1200
Ala Pro Thr Leu Asp Lys Leu Ile Glu Ala Arg Arg Tyr Phe Ala Tyr
    355             360             365 ggt cct ggc cat gag tac tcc ggc aat acc gag gcc gtc tac gcc tat    1248
Gly Pro Gly His Glu Tyr Ser Gly Asn Thr Glu Ala Val Tyr Ala Tyr
370             375             380             385 gtg cgc gaa ggg ctt agc act gtg ccg ggt acc ggt ctg gtg atg ctg    1296
Val Arg Glu Gly Leu Ser Thr Val Pro Gly Thr Gly Leu Val Met Leu
                390             395             400 ata tcg ggt cga aac tgg ggt ggt cag cag tcg ttc acc atc aac agc    1344
Ile Ser Gly Arg Asn Trp Gly Gly Gln Gln Ser Phe Thr Ile Asn Ser
            405             410             415 cac cag ccg aat acc acc ttt tac gat tat acc ggc aat gtt agc ggc    1392
His Gln Pro Asn Thr Thr Phe Tyr Asp Tyr Thr Gly Asn Val Ser Gly
        420             425             430 acg gtg acc acc aat gcg cag ggc tat ggc agc ttc ccg gtc act atg    1440
Thr Val Thr Thr Asn Ala Gln Gly Tyr Gly Ser Phe Pro Val Thr Met
    435             440             445 acg gaa agt acc ggt tgg tca gtc tgg gta cca caa tcc aat ggt ggc    1488
Thr Glu Ser Thr Gly Trp Ser Val Trp Val Pro Gln Ser Asn Gly Gly
450             455             460             465 act cag ccg gga tcc att acc ctg cgg atg acc aag gat gtt ggc tat    1536
Thr Gln Pro Gly Ser Ile Thr Leu Arg Met Thr Lys Asp Val Gly Tyr
                470             475             480 ggc ttt tcg ttg ttc ttc acc ggc agc agt gcg gaa ctg acc aac tgg    1584
Gly Phe Ser Leu Phe Phe Thr Gly Ser Ser Ala Glu Leu Thr Asn Trp
            485             490             495 ggc ggt ggt att gaa ggc acc tgg aca tcc ggt aat gtc tgg gaa gtg    1632
Gly Gly Gly Ile Glu Gly Thr Trp Thr Ser Gly Asn Val Trp Glu Val
        500             505             510 acc atc ccg gat cc                                                 1646
Thr Ile Pro Asp
    515

<210> SEQ ID NO 2
<211> LENGTH: 548
<212> TYPE: PRT
<213> ORGANISM: Bacillus sp.
<220> FEATURE:
<221> NAME/KEY: SIGNAL
<222> LOCATION: (1)...(31)

<400> SEQUENCE: 2

Met Gln Asn Thr Ala Lys Asn Ser Ile Trp Gln Arg Val Arg His Ser
    -30             -25             -20

Ala Ile Ala Leu Ser Ala Leu Ser Leu Ser Phe Gly Leu Gln Ala Ser
-15             -10              -5              1

Glu Leu Pro Gln Ile Pro Pro Gln Gln Val Asn Asn Thr Met Tyr Gln
                5               10              15

Ala Phe Tyr Trp Asp Ala Tyr Pro Gly Leu Trp Ala Asn Leu Pro Ala
            20              25              30

Met Ala Ala Pro Leu Ala Glu Arg Gly Ile Thr Ser Met Trp Leu Pro
        35              40              45

Pro Ala Ala Lys Gly Met Asn Gly Thr Phe Ser Val Gly Tyr Asp Val
    50              55              60              65

Tyr Asp Phe Trp Asp Leu Gly Glu Phe Asn Gln Lys Gly Thr Ala
                70              75              80

Thr Arg Tyr Gly Thr Arg Gln Gln Leu Gln Gln Ala Leu Ser Ala Leu
```

-continued

```
                    85                  90                  95
Asp Gln Leu Gly Ile Gln Ala Tyr Phe Asp Val Val Phe Asn His Arg
            100                 105                 110
Met Gly Ala Asp Ala Gln Glu Asn Ile Pro Gly Phe Gly Leu Ala Trp
            115                 120                 125
Thr Glu Tyr His Leu Gln Gly Arg Gln Ala His Tyr Thr Gln Gln Asn
130                 135                 140                 145
Trp Gly Tyr Leu Trp His Asp Phe Asp Trp Asn Trp Thr Ala Phe Asn
                150                 155                 160
Gly Ser Asp Asn Gln Leu Tyr Pro Gly Lys Trp Trp Gly Asn Thr Phe
            165                 170                 175
His Phe Pro Tyr Leu Met Gly Glu Asp Val Asp Tyr Asn Arg Phe Glu
            180                 185                 190
Val Gln Gln Glu Met Lys Ala Trp Gly Glu Trp Ile Ile Asn Ser Val
            195                 200                 205
Gly Phe Ser Gly Phe Arg Met Asp Ala Ile Ala His Val Asp Thr Asp
210                 215                 220                 225
Phe Thr Arg Asp Trp Ile Asn His Val Gln Trp Ala Thr Ser Glu Asp
                230                 235                 240
Val Phe Phe Val Ala Glu Ala Trp Val Ser Asp Ile Asn Gly Tyr Leu
            245                 250                 255
Asp Ala Val Asn Thr Pro His Leu Arg Ala Phe Asp Phe Asn Leu Arg
            260                 265                 270
Glu Asp Phe Val Ala Leu Ser Ser Gly Ser Lys Asp Met Arg Trp Trp
            275                 280                 285
Gly Gly Leu Val Asn Ser Gln His Arg Asp Arg Ala Val Thr Phe Val
290                 295                 300                 305
Asp Asn His Asp Thr Ser Arg Ala Gly Asn Pro Tyr Gly Met Pro Gln
                310                 315                 320
Val Ile Asn Tyr Lys Asn Gln Ala Tyr Ala Tyr Ile Leu Leu Arg Glu
            325                 330                 335
His Gly Val Pro Thr Val Phe Ala Arg Asp Tyr Asp Glu Phe Gly Met
            340                 345                 350
Ala Pro Thr Leu Asp Lys Leu Ile Glu Ala Arg Arg Tyr Phe Ala Tyr
            355                 360                 365
Gly Pro Gly His Glu Tyr Ser Gly Asn Thr Glu Ala Val Tyr Ala Tyr
370                 375                 380                 385
Val Arg Glu Gly Leu Ser Thr Val Pro Gly Thr Gly Leu Val Met Leu
                390                 395                 400
Ile Ser Gly Arg Asn Trp Gly Gly Gln Gln Ser Phe Thr Ile Asn Ser
            405                 410                 415
His Gln Pro Asn Thr Thr Phe Tyr Asp Tyr Thr Gly Asn Val Ser Gly
            420                 425                 430
Thr Val Thr Thr Asn Ala Gln Gly Tyr Gly Ser Phe Pro Val Thr Met
            435                 440                 445
Thr Glu Ser Thr Gly Trp Ser Val Trp Val Pro Gln Ser Asn Gly Gly
450                 455                 460                 465
Thr Gln Pro Gly Ser Ile Thr Leu Arg Met Thr Lys Asp Val Gly Tyr
                470                 475                 480
Gly Phe Ser Leu Phe Phe Thr Gly Ser Ser Ala Glu Leu Thr Asn Trp
            485                 490                 495
Gly Gly Gly Ile Glu Gly Thr Trp Thr Ser Gly Asn Val Trp Glu Val
            500                 505                 510
```

Thr Ile Pro Asp
    515

<210> SEQ ID NO 3
<211> LENGTH: 1764
<212> TYPE: DNA
<213> ORGANISM: Bacillus sp.
<220> FEATURE:
<221> NAME/KEY: CDS
<222> LOCATION: (1)...(1764)
<221> NAME/KEY: sig_peptide
<222> LOCATION: (1)...(93)
<221> NAME/KEY: mat_peptide
<222> LOCATION: (94)...(1764)

<400> SEQUENCE: 3

```
atg caa aac aca gcg aaa aac tcc atc tgg cag agg gtg cgc cac agc        48
Met Gln Asn Thr Ala Lys Asn Ser Ile Trp Gln Arg Val Arg His Ser
    -30             -25                 -20 gcc att gcc tta tcc gct ctc agt tta tcc ttt ggc ctg cag gcc agc        96
Ala Ile Ala Leu Ser Ala Leu Ser Leu Ser Phe Gly Leu Gln Ala Ser
-15             -10                 -5                   1 gag tta cca caa att cca cca cag cag gtg aac aac acc atg tac cag       144
Glu Leu Pro Gln Ile Pro Pro Gln Gln Val Asn Asn Thr Met Tyr Gln
            5                  10                  15 gca ttt tat tgg gat gcc tac cct ggc ctt tgg gcc aat tta ccg gcc       192
Ala Phe Tyr Trp Asp Ala Tyr Pro Gly Leu Trp Ala Asn Leu Pro Ala
         20                  25                  30 atg gcg gcc cct ttg gcc gag cgt ggc att acc tcg atg tgg ttg ccg       240
Met Ala Ala Pro Leu Ala Glu Arg Gly Ile Thr Ser Met Trp Leu Pro
 35                  40                  45 ccc gcc gcc aaa ggc atg aat ggt act ttc agt gtc ggt tac gat gta       288
Pro Ala Ala Lys Gly Met Asn Gly Thr Phe Ser Val Gly Tyr Asp Val
 50                  55                  60                  65 tac gat ttc tgg gat ctg ggc gag ttt aac caa aaa ggc acc acc gcc       336
Tyr Asp Phe Trp Asp Leu Gly Glu Phe Asn Gln Lys Gly Thr Thr Ala
             70                  75                  80 acc cgt tac ggt act cgt cag cag ctg caa caa gca ctg agt gct ctg       384
Thr Arg Tyr Gly Thr Arg Gln Gln Leu Gln Gln Ala Leu Ser Ala Leu
         85                  90                  95 gac caa ctg ggt att cag gcc tat ttt gat gtg gtg ttt aac cac cgc       432
Asp Gln Leu Gly Ile Gln Ala Tyr Phe Asp Val Val Phe Asn His Arg
            100                 105                 110 atg ggc gcc gat gca cag gag aat att cct ggc ttt ggc ctg gcc tgg       480
Met Gly Ala Asp Ala Gln Glu Asn Ile Pro Gly Phe Gly Leu Ala Trp
115                 120                 125 acc gag tat cat ctg caa ggt cgt cag gcg cat tat acc cag caa aac       528
Thr Glu Tyr His Leu Gln Gly Arg Gln Ala His Tyr Thr Gln Gln Asn
130                 135                 140                 145 tgg ggc tac ttg tgg cac gac ttt gac tgg aac tgg acc gcg ttt aat       576
Trp Gly Tyr Leu Trp His Asp Phe Asp Trp Asn Trp Thr Ala Phe Asn
                150                 155                 160 ggc tcc gac aat cag ctc tac ccc gga aaa tgg tgg ggc aat acc ttc       624
Gly Ser Asp Asn Gln Leu Tyr Pro Gly Lys Trp Trp Gly Asn Thr Phe
            165                 170                 175 cac ttc cct tat ttg atg ggt gag gat gtc gat tac aac cgc ttt gaa       672
His Phe Pro Tyr Leu Met Gly Glu Asp Val Asp Tyr Asn Arg Phe Glu
        180                 185                 190 gtg cag cag gaa atg aaa gcc tgg ggc gag tgg atc atc aac agc gtt       720
Val Gln Gln Glu Met Lys Ala Trp Gly Glu Trp Ile Ile Asn Ser Val
    195                 200                 205
```

```
ggc ttt agc ggc ttt cgg atg gat gcc atc gcc cat gtc gat acc gat       768
Gly Phe Ser Gly Phe Arg Met Asp Ala Ile Ala His Val Asp Thr Asp
210                 215                 220                 225 ttt acc cgt gac tgg atc aat cac gtg cag tgg gcc acc agt gag gat       816
Phe Thr Arg Asp Trp Ile Asn His Val Gln Trp Ala Thr Ser Glu Asp
            230                 235                 240 gtg ttc ttt gtc gct gaa gcc tgg gtc agt gat atc aac ggc tat ctg       864
Val Phe Phe Val Ala Glu Ala Trp Val Ser Asp Ile Asn Gly Tyr Leu
                245                 250                 255 gat gca gtc aat acg ccg cat ttg cgc gct ttt gat ttc aat ttg cgc       912
Asp Ala Val Asn Thr Pro His Leu Arg Ala Phe Asp Phe Asn Leu Arg
            260                 265                 270 gaa gac ttc gtt gct tta agc agc ggt agc aaa gac atg cgt tgg tgg       960
Glu Asp Phe Val Ala Leu Ser Ser Gly Ser Lys Asp Met Arg Trp Trp
275                 280                 285 ggc ggt ctg gtc aat agc cag cac cgt gat cgg gcg tca act ttt gtc      1008
Gly Gly Leu Val Asn Ser Gln His Arg Asp Arg Ala Val Thr Phe Val
290                 295                 300                 305 gat aac cac gat acc agc cgg gcc ggc aac cct tat ggc atg ccg cag      1056
Asp Asn His Asp Thr Ser Arg Ala Gly Asn Pro Tyr Gly Met Pro Gln
            310                 315                 320 gtg atc aac tac aag aac cag gcc tac gct tac att ctg ttg cgt gag      1104
Val Ile Asn Tyr Lys Asn Gln Ala Tyr Ala Tyr Ile Leu Leu Arg Glu
                325                 330                 335 cat ggg gtg ccg act gtg ttt gcc cgc gat tac gac gaa ttt ggc atg      1152
His Gly Val Pro Thr Val Phe Ala Arg Asp Tyr Asp Glu Phe Gly Met
            340                 345                 350 gcg cca acg ctg gat aaa ttg att gag gcg cgc cgc tac ttt gct tat      1200
Ala Pro Thr Leu Asp Lys Leu Ile Glu Ala Arg Arg Tyr Phe Ala Tyr
355                 360                 365 ggt cct ggc cat gag tac tcc ggc aat acc gag gcc gtc tac gcc tat      1248
Gly Pro Gly His Glu Tyr Ser Gly Asn Thr Glu Ala Val Tyr Ala Tyr
370                 375                 380                 385 gtg cgc gaa ggg ctt agc act gtg ccg ggt acc ggt ctg gtg atg ctg      1296
Val Arg Glu Gly Leu Ser Thr Val Pro Gly Thr Gly Leu Val Met Leu
            390                 395                 400 ata tcg ggt cga aac tgg ggt ggt cag cag tcg ttc acc atc aac agc      1344
Ile Ser Gly Arg Asn Trp Gly Gly Gln Gln Ser Phe Thr Ile Asn Ser
                405                 410                 415 cac cag ccg aat acc acc ttt tac gat tat acc ggc aat gtt agc ggc      1392
His Gln Pro Asn Thr Thr Phe Tyr Asp Tyr Thr Gly Asn Val Ser Gly
            420                 425                 430 acg gtg acc acc aat gcg cag ggc tat ggc agc ttc ccg gtc act atg      1440
Thr Val Thr Thr Asn Ala Gln Gly Tyr Gly Ser Phe Pro Val Thr Met
435                 440                 445 acg gaa agt acc ggt tgg tca gtc tgg gta cca caa tcc aat ggt ggc      1488
Thr Glu Ser Thr Gly Trp Ser Val Trp Val Pro Gln Ser Asn Gly Gly
450                 455                 460                 465 act cag ccg gga tcc att acc ctg cgg atg acc aag gat gtt ggc tat      1536
Thr Gln Pro Gly Ser Ile Thr Leu Arg Met Thr Lys Asp Val Gly Tyr
            470                 475                 480 ggc ttt tcg ttg ttc ttc acc ggc agc agt gcg gaa ctg acc aac tgg      1584
Gly Phe Ser Leu Phe Phe Thr Gly Ser Ser Ala Glu Leu Thr Asn Trp
                485                 490                 495 ggc ggt ggt att gaa ggc acc tgg aca tcc ggt aat gtc tgg gaa gtg      1632
Gly Gly Gly Ile Glu Gly Thr Trp Thr Ser Gly Asn Val Trp Glu Val
            500                 505                 510 acc atc ccg gat ccg ggc aac ttt gaa tgg aaa acc cgt aaa ggc cca      1680
Thr Ile Pro Asp Pro Gly Asn Phe Glu Trp Lys Thr Arg Lys Gly Pro
515                 520                 525
```

-continued

```
acc ggt ggc agt ggt cag gac tgg gaa agt ggc agc aac cac aat cag      1728
Thr Gly Gly Ser Gly Gln Asp Trp Glu Ser Gly Ser Asn His Asn Gln
530                 535                 540                 545 acc aat ttg cac ccc agt ttt aat ggt ggg ttt taa                      1764
Thr Asn Leu His Pro Ser Phe Asn Gly Gly Phe
                550                 555
```

<210> SEQ ID NO 4
<211> LENGTH: 587
<212> TYPE: PRT
<213> ORGANISM: Bacillus sp.
<220> FEATURE:
<221> NAME/KEY: SIGNAL
<222> LOCATION: (1)...(31)

<400> SEQUENCE: 4

```
Met Gln Asn Thr Ala Lys Asn Ser Ile Trp Gln Arg Val Arg His Ser
        -30                 -25                 -20

Ala Ile Ala Leu Ser Ala Leu Ser Leu Ser Phe Gly Leu Gln Ala Ser
-15                 -10                  -5                   1

Glu Leu Pro Gln Ile Pro Pro Gln Val Asn Asn Thr Met Tyr Gln
                 5                  10                  15

Ala Phe Tyr Trp Asp Ala Tyr Pro Gly Leu Trp Ala Asn Leu Pro Ala
                20                  25                  30

Met Ala Ala Pro Leu Ala Glu Arg Gly Ile Thr Ser Met Trp Leu Pro
        35                  40                  45

Pro Ala Ala Lys Gly Met Asn Gly Thr Phe Ser Val Gly Tyr Asp Val
50                  55                  60                  65

Tyr Asp Phe Trp Asp Leu Gly Glu Phe Asn Gln Lys Gly Thr Thr Ala
                70                  75                  80

Thr Arg Tyr Gly Thr Arg Gln Gln Leu Gln Gln Ala Leu Ser Ala Leu
                85                  90                  95

Asp Gln Leu Gly Ile Gln Ala Tyr Phe Asp Val Val Phe Asn His Arg
        100                 105                 110

Met Gly Ala Asp Ala Gln Glu Asn Ile Pro Gly Phe Gly Leu Ala Trp
        115                 120                 125

Thr Glu Tyr His Leu Gln Gly Arg Gln Ala His Tyr Thr Gln Gln Asn
130                 135                 140                 145

Trp Gly Tyr Leu Trp His Asp Phe Asp Trp Asn Trp Thr Ala Phe Asn
                150                 155                 160

Gly Ser Asp Asn Gln Leu Tyr Pro Gly Lys Trp Trp Gly Asn Thr Phe
                165                 170                 175

His Phe Pro Tyr Leu Met Gly Glu Asp Val Asp Tyr Asn Arg Phe Glu
                180                 185                 190

Val Gln Gln Glu Met Lys Ala Trp Gly Glu Trp Ile Ile Asn Ser Val
        195                 200                 205

Gly Phe Ser Gly Phe Arg Met Asp Ala Ile Ala His Val Asp Thr Asp
210                 215                 220                 225

Phe Thr Arg Asp Trp Ile Asn His Val Gln Trp Ala Thr Ser Glu Asp
                230                 235                 240

Val Phe Phe Val Ala Glu Ala Trp Val Ser Asp Ile Asn Gly Tyr Leu
                245                 250                 255

Asp Ala Val Asn Thr Pro His Leu Arg Ala Phe Asp Phe Asn Leu Arg
        260                 265                 270

Glu Asp Phe Val Ala Leu Ser Ser Gly Ser Lys Asp Met Arg Trp Trp
        275                 280                 285
```

```
Gly Gly Leu Val Asn Ser Gln His Arg Asp Arg Ala Val Thr Phe Val
290                 295                 300                 305

Asp Asn His Asp Thr Ser Arg Ala Gly Asn Pro Tyr Gly Met Pro Gln
                310                 315                 320

Val Ile Asn Tyr Lys Asn Gln Ala Tyr Ala Tyr Ile Leu Leu Arg Glu
                325                 330                 335

His Gly Val Pro Thr Val Phe Ala Arg Asp Tyr Asp Glu Phe Gly Met
                340                 345                 350

Ala Pro Thr Leu Asp Lys Leu Ile Glu Ala Arg Arg Tyr Phe Ala Tyr
355                 360                 365

Gly Pro Gly His Glu Tyr Ser Gly Asn Thr Glu Ala Val Tyr Ala Tyr
370                 375                 380                 385

Val Arg Glu Gly Leu Ser Thr Val Pro Gly Thr Gly Leu Val Met Leu
                390                 395                 400

Ile Ser Gly Arg Asn Trp Gly Gly Gln Gln Ser Phe Thr Ile Asn Ser
                405                 410                 415

His Gln Pro Asn Thr Thr Phe Tyr Asp Tyr Thr Gly Asn Val Ser Gly
                420                 425                 430

Thr Val Thr Thr Asn Ala Gln Gly Tyr Gly Ser Phe Pro Val Thr Met
435                 440                 445

Thr Glu Ser Thr Gly Trp Ser Val Trp Val Pro Gln Ser Asn Gly Gly
450                 455                 460                 465

Thr Gln Pro Gly Ser Ile Thr Leu Arg Met Thr Lys Asp Val Gly Tyr
                470                 475                 480

Gly Phe Ser Leu Phe Phe Thr Gly Ser Ser Ala Glu Leu Thr Asn Trp
                485                 490                 495

Gly Gly Gly Ile Glu Gly Thr Trp Thr Ser Gly Asn Val Trp Glu Val
                500                 505                 510

Thr Ile Pro Asp Pro Gly Asn Phe Glu Trp Lys Thr Arg Lys Gly Pro
515                 520                 525

Thr Gly Gly Ser Gly Gln Asp Trp Glu Ser Gly Ser Asn His Asn Gln
530                 535                 540                 545

Thr Asn Leu His Pro Ser Phe Asn Gly Gly Phe
                550                 555
```

US 7,078,213 B1

ALKALINE BACILLUS AMYLASE

CROSS-REFERENCE TO RELATED APPLICATIONS

This application is a continuation-in-part of application Ser. No. 09/249,558 filed on Feb. 12, 1999 now abandoned and claims priority under 35 U.S.C. 119 of Danish application no. 0228/98 filed on Feb. 18, 1998, and U.S. provisional application No. 60/146,297, filed on Feb. 27, 1998, the contents of which are fully incorporated by reference.

FIELD OF INVENTION

The present invention relates to amylases having improved washing performance in an alkaline detergent solution at low temperature.

BACKGROUND OF THE INVENTION

For a number of years α-amylase enzymes have been used for a variety of different purposes, the most important of which are starch liquefaction, textile desizing, starch modification in the paper and pulp industry, and for brewing and baking. A further use of α-amylases, which is becoming increasingly important is the removal of starchy stains during washing with a detergent at alkaline pH.

Examples of commercial α-amylase products are Termamyl®, BAN® and Fungamyl®, all available from Novo Nordisk A/S, Denmark. These and similar products from other commercial sources have an acidic to a neutral pH optimum, typically in the range of from pH 5 to pH 7.5, and they do not display optimal activity in detergent solutions at alkaline pH.

WO 95/26397 discloses an α-amylase from a Bacillus strain which has optimum activity at pH 8. WO 96/23873 describes variants of Bacillus amylases with improved performance under washing conditions.

U.S. Pat. No. 5,147,796 describes an alkaline pullulanase having alpha-amylase activity. FIG. 2b of the document shows optimum amylase activity at pH 8–8.5.

M. Takagi et al., J. Ferment. Bioeng., vol 81, No. 6, 557–559 (1996) describe an alkaliphilic alpha-amylase-pullulanase from Bacillus sp. The enzyme has optimum amylase activity at pH 9, but the activity drops rapidly at higher pH, and the activity at pH 10 is lower than at pH 7.

It is an object of the present invention to provide novel α-amylases with improved performance in alkaline solutions, especially in alkaline detergent solutions at pH around 9–11.

SUMMARY OF THE INVENTION

The present invention provides alpha-amylase which is:
a) a polypeptide produced by Bacillus sp. NCIMB 40916, or
b) a polypeptide having an amino acid sequence as shown in positions 1–556 of SEQ ID NO: 4, or
c) a polypeptide encoded by the alpha-amylase encoding part of the DNA sequence cloned into a plasmid present in Escherichia coli DSM 13001, or
d) an analogue of the polypeptide defined in (a) or (b) which:
  i) is at least 60% homologous with said polypeptide, or
  ii) is derived from said polypeptide by substitution, deletion and/or insertion of one or several amino acids.

In an embodiment of the invention the alpha-amylase is the truncated mature alpha-amylase shown in SEQ ID NO: 2 (i.e., amino acids 1–517) encoded by nucleotides 94–1646 of the DNA sequence shown in SEQ ID NO: 1 and deposited as Escherichia coli DSM 12662.

In another aspect, the invention provides an α-amylase having one or more of the following characteristics:
an activity at pH 10.5 which is at least two times higher than the activity at pH 7.3 when measured at 37° C.
an activity at pH 9.5 which is at least 4 times higher than the activity at pH 7.3 when measured at 37° C.
an optimum pH of about 9.5 when measured at 37° C.
a thermostability such that it retains more than 90% of its activity after 20 minutes incubation at 25° C. in a solution of 3 g/l of a test detergent containing 20% STPP, 25% $Na_2SO_4$, 15% $Na_2CO_3$, 20% LAS, 5% $C_{12}$–$C_{15}$ alcohol ethoxylate, 5% $Na_2Si_2O_5$; 0.3% NaCl at pH 10.5 and 6 degrees German hardness, and retains less than 90% of its activity after 20 minutes incubation at 30° C. in the same solution.
a molecular weight of about 55 kDa as determined by SDS-PAGE.
an iso-electric point of about 5 as determined by isoelectric focusing.

The invention also provides an isolated DNA sequence which encodes an alpha-amylase, wherein the alpha-amylase is that described above, or wherein the DNA sequence comprises:
a) the DNA sequence shown in positions 94–1764 of SEQ ID NO: 3, or
b) an analogue of the DNA sequence defined in a) which
  i) is at least 60% homologous with said DNA sequence, or
  ii) hybridizes with said DNA sequence at least 55° C.

Other aspects of the invention provide a recombinant expression vector comprising the DNA sequence, and a cell transformed with the DNA sequence or the recombinant expression vector.

The invention also provides a method for producing an alpha-amylase by cultivating the cell and a detergent composition comprising said alpha-amylase.

BRIEF DESCRIPTION OF DRAWINGS

The present invention is further illustrated with reference to the accompanying drawings, in which.

DETAILED DESCRIPTION OF THE INVENTION

Microbial Source

Figure 1:
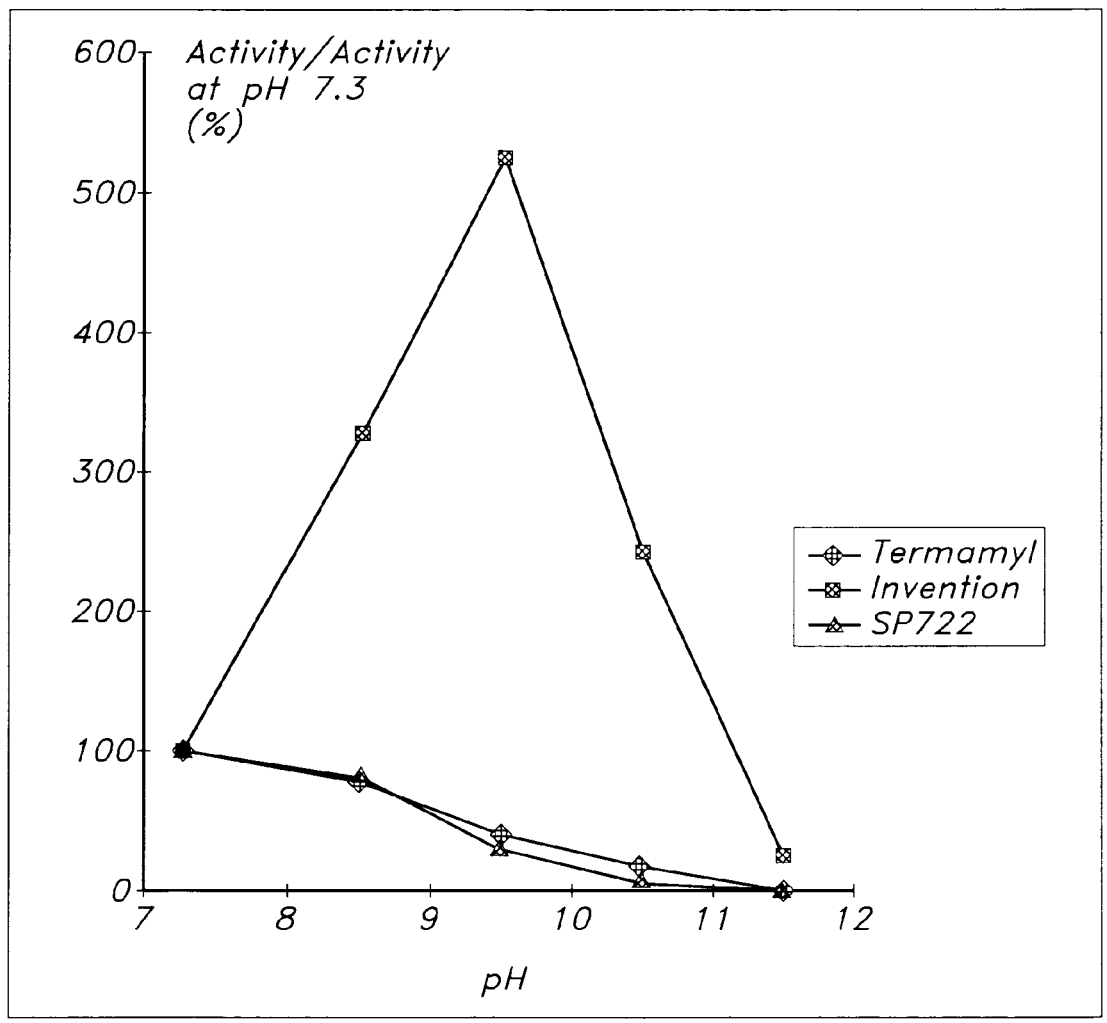
FIG. 1 shows a pH activity profile of the amylase from NCIMB 40916 compared to two prior-art amylases (SP722 and Termamyl).

The alpha-amylase of the invention may be derived from a strain of Bacillus. A preferred strain is Bacillus sp. NCIMB 40916. This strain was deposited on 28 Jan. 1998 by the inventors under the terms of the Budapest Treaty on the International Recognition of the Deposit of Microorganisms for the Purposes of Patent Procedure at the National Collections of Industrial and Marine Bacteria Limited (NCIMB), 23 St. Machar Drive, Aberdeen AB2 1RY, Scotland, United Kingdom. An *Escherichia coli* strain termed JA388 containing the truncated alpha amylase gene shown in SEQ ID NO: 1 cloned in plasmid pJA388 has also been deposited on 3 Feb. 1999 under the terms of the Budapest Treaty with the Deutshe Sammmlung von Microorganismen und Zellkulturen GmbH (DSMZ), Mascheroder Weg 1b, D-38124 Braunschweig DE, and given the accession number DSM 12662. Further, an *Escherichia coli* strain termed NN049489 containing the full length alpha amylase gene shown in SEQ ID NO: 3 cloned into plasmid pJA386 has also been deposited on 17 Aug. 1999, under the terms of the Budapest Treaty with the Deutshe Sammmlung von Microorganismen und Zelikulturen GmbH (DSMZ), Mascheroder Weg 1b, D-38124 Braunschweig DE, and given the accession number DSM 13001. It is believed that SEQ ID NO: 3 and the deposited sequence are identical.

Production of alpha-amylase

The alpha-amylase of the invention can be produced by cultivating a suitable amylase-producing strain of *Bacillus* or the transformed host cell of the invention in a suitable nutrient medium, and recovering the alpha-amylase from the culture medium.

The medium used to cultivate the cells may be any conventional medium suitable for growing the host cell in question and obtaining expression of the α-amylase of the invention. Suitable media are available from commercial suppliers or may be prepared according to published recipes (e.g. as described in catalogues of the American Type Culture Collection).

The α-amylase secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Properties of alpha-amylase

A preferred alpha-amylase is derived from *Bacillus* sp. NCIMB 40916. It can be produced as described in the examples. The full length amino acid sequence of the amylase and the DNA encoding it are shown in SEQ ID NO: 3 and 4. The DNA and amino acid sequence of the truncated alpha-amylase is shown in SEQ ID NO: 1 and 3, respectively. The following characteristics were found for the full length amylase of the invention (purified alpha-amylase from NCIMB 40916):

A molecular weight of approximately 55 kDa as determined by SDS-PAGE using a Novex, 4–25% gradient gel.

A pI of approximately 5 was determined by isoelectric focusing (Ampholine PAG, pH 3.5–9.5).

A pH-activity curve is shown in FIG. 1, taking the activity at pH 7.3 as 100%. It was determined using the Phadebas assay using 50 mM Britten-Robinson buffer adjusted to various pH-values. For reference, the pH profiles of two prior-art *Bacillus* amylases (Termamyl derived from *B. licheniformis* and SP722 produced according to WO 95/26397) were measured under the same conditions are also shown in FIG. 1. FIG. 1 shows that the amylase of the invention has about 10 times higher activity than the two prior-art amylases at pH 9.5. FIG. 1 also shows that the optimum activity is about pH 9.5.

Figure 2:
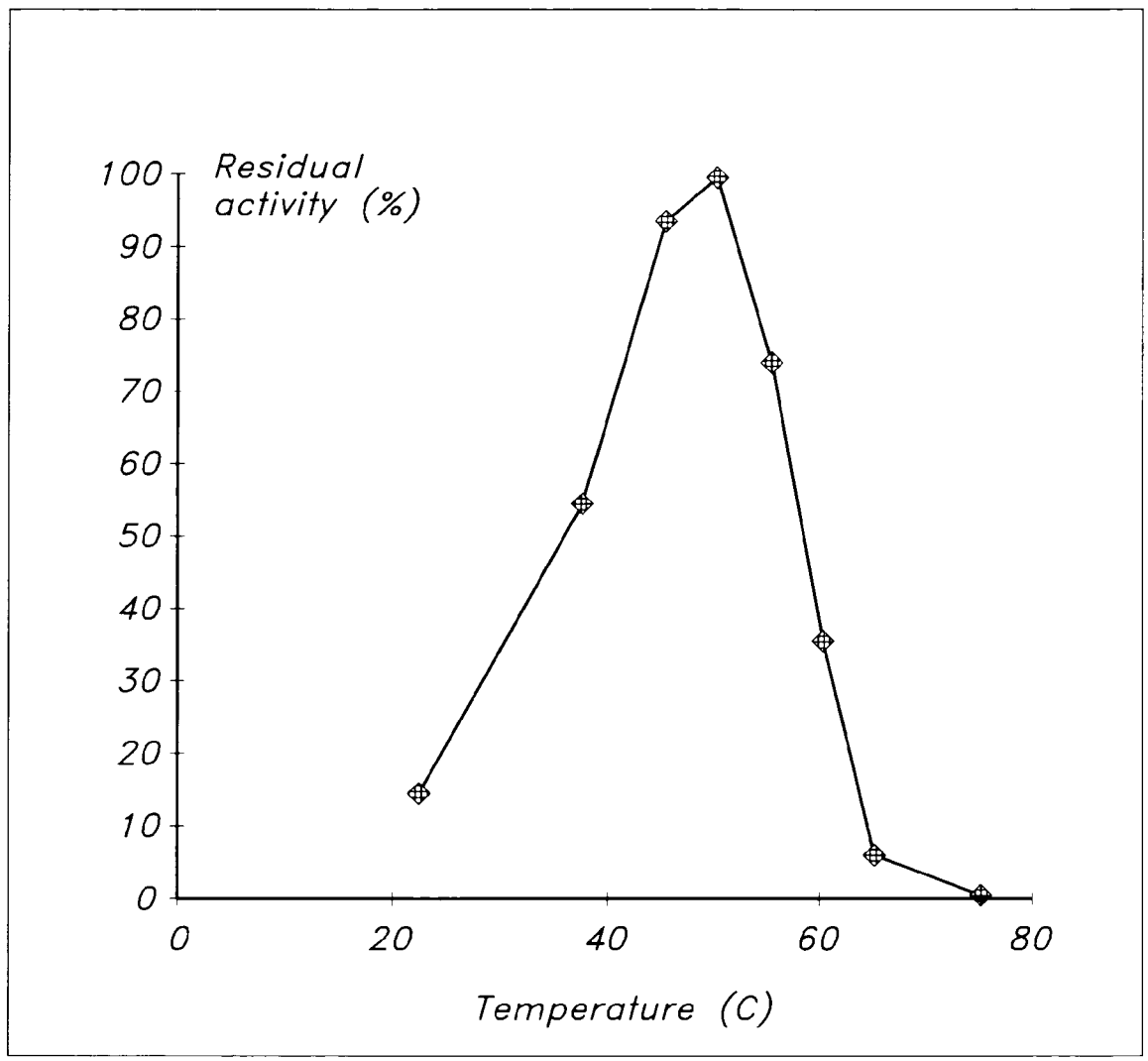
FIG. 2 shows a temperature activity profile of the amylase from NCIMB 40916.

A temperature-activity curve was measured using the Phadebas assay at various temperatures with 50 mM Britten-Robinson buffer adjusted to pH 9.5. The results are shown in FIG. 2. It is seen from FIG. 2 that the amylase of the invention has optimum activity at about 50° C.

Figure 3:
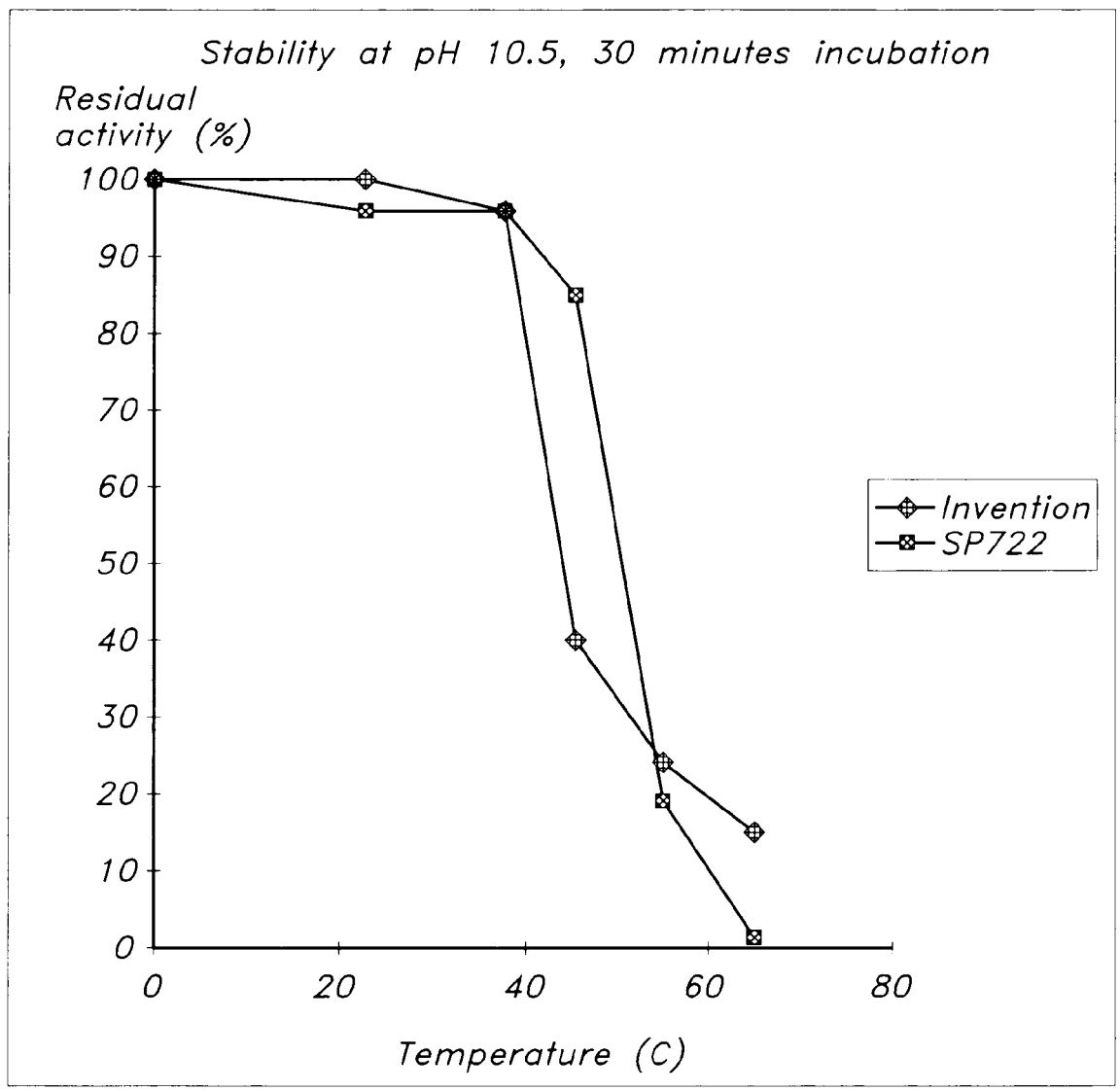
FIG. 3 shows the stability of the amylase from NCIMB 40916 after incubation at various temperatures.

Stability of the amylase was measured at pH 10.5 (50 mM CAPS) at 22, 37, 45, 55 and 65° C. after 30 minutes incubation. The enzyme was diluted to 40 NU/ml in buffer and 25 microlitre sample was incubated at the respective temperatures. After 30 minutes, the samples was chilled on ice and residual activity was determined. A stability profile of the amylase of the invention and a prior-art amylase (SP722) is shown in FIG. 3.

Stability was tested by incubating 40 NU/ml of amylase in a solution of 3 g/l of the A/P model detergent described above, at pH 10.5 and 6° dH (German hardness, Ca:Mg 2:1). After the incubation, the residual activity was measured by Phadebas at pH 7.3. The results were 95% residual activity after incubation at 25° C., and 87% at 30° C.

Homology of Polypeptide and DNA Sequence

The amino acid sequence homology may be determined as the degree of identity between the two sequences indicating a derivation of the first sequence from the second. The homology may suitably be determined by means of computer programs known in the art. Thus, FASTA provided in GCG version 8 (Needleman, S. B. and Wunsch, C. D., (1970), Journal of Molecular Biology, 48, 443–453) may be used with the following settings: Scoring matrix: GenRunData:blosum50.cmp, Variable pamfactor used Gap creation penalty: 12, Gap extension penalty: 2. Alternatively, Gap from GCG version 9 may be used with a translated version 8 peptide scoring matrix, a gap creation penalty of 30, a gap extension penalty of 1 using ntol's matrix (http://plasmid/~bioweb/matrix/) without end gap penalty.

The amino acid sequence exhibits a degree of identity preferably of at least 60%, preferably at least 70%, more preferably at least 80%, especially at least 90% or at least 95%, with the amino acid sequence shown in positions 1–556 of SEQ ID NO: 4.

The DNA sequence homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the following default parameters: GAP creation penalty of 5.0 and GAP extension penalty of 0.3, default scoring matrix. GAP uses the method of Needleman/Wunsch/Sellers to make alignments.

The DNA construct of the present invention comprises a DNA sequence exhibiting a degree of identity preferably of at least 60%, preferably at least 70%, more preferably at least 80%, especially at least 90% or at least 95%, with the nucleic acid sequence shown in positions 94–1764 of SEQ ID NO: 3.

Hybridization

The hybridization is used to indicate that a given DNA sequence is analogous to a nucleotide probe corresponding to SEQ ID NO: 3. The hybridization conditions are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5× Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at approx. 45° C. The filter is then washed two times for 30 minutes in 2×SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using a x-ray film.

Recombinant Expression Vector

The expression vector of the invention typically includes control sequences encoding a promoter, operator, ribosome binding site, translation initiation signal, and, optionally, a repressor gene or various activator genes.

The recombinant expression vector carrying the DNA sequence encoding the α-amylase of the invention may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g. when using certain bacteria as host cells, it is generally preferred that the expression is extracellular.

Procedures suitable for constructing vectors of the invention encoding an α-amylase, and containing the promoter, terminator and other elements, respectively, are well known to persons skilled in the art [cf., for instance, Sambrook et al. (1989)].

Host Cells

The cell of the invention, either comprising a DNA construct or an expression vector of the invention as defined above, is advantageously used as a host cell in the recombinant production of the α-amylase of the invention. The cell may be transformed with the DNA construct of the invention encoding the amylase, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of bacterial host cells which, on cultivation, are capable of producing the enzyme of the invention are gram-positive bacteria such as strains of *Bacillus*, such as strains of *B. subtilis*, *B. licheniformis*, *B. lentus*, *B. clausii*, *B. brevis*, *B. stearothermophilus*, *B. alkalophilus*, *B. amyloliquefaciens*, *B. coagulans*, *B. circulans*, *B. lautus*, *B. megaterium* or *B. thuringiensis*, or strains of *Streptomyces*, such as *S. lividans* or *S. murinus*, or gram-negative bacteria such as *Escherichia coli*. The transformation of the bacteria may be effected by protoplast transformation, electroporation, conjugation, or by using competent cells in a manner known per se (cf. Sambrook et al., supra).

The yeast organism may favourably be selected from a species of *Saccharomyces* or *Schizosaccharomyces*, e.g. *Saccharomyces cerevisiae*. The filamentous fungus may advantageously belong to a species of *Aspergillus*, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

Industrial Applications

Owing to their activity at alkaline pH values, the α-amylases of the invention are well suited for use in a variety of industrial processes, in particular the enzyme finds potential applications as a component in detergents, e.g. laundry and hard surface cleaning detergent compositions, but it may also be useful in the production of sweeteners and ethanol from starch. Thus, it may be used in conventional starch-converting processes, such as liquefaction and saccharification processes described in U.S. Pat. No. 3,912,590 and EP patent publications Nos. 252,730 and 63,909.

The alkaline α-amylase of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The α-amylase of the invention is especially useful in a process for producing a papermaking pulp from starch-coated printed paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The α-amylases of the invention may also be very useful in modifying starch where enzymatically modified starch is used in papermaking together with alkaline fillers such as calcium carbonate, kaolin and clays. With the alkaline α-amylases of the invention it becomes possible to modify the starch in the presence of the filler thus allowing for a simpler integrated process.

The α-amylase of the invention may also be very useful in textile desizing. In the textile processing industry, α-amylases are traditionally used as auxiliaries in the desizing process to facilitate the removal of starch-containing size which has served as a protective coating on weft yarns during weaving. Complete removal of the size coating after weaving is important to ensure optimum results in the subsequent processes, in which the fabric is scoured, bleached and dyed. Enzymatic starch break-down is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fiber damage because of the rather aggressive chemicals used. Accordingly, it would be desirable to use the α-amylases of the invention as they have an improved performance in alkaline solutions. The α-amylases may be used alone or in combination with a cellulase when desizing cellulose-containing fabric or textile.

The α-amylases of the invention may also be very useful in a beer-making process; the α-amylases will typically be added during the mashing process.

Detergent Compositions

According to the invention, the α-amylase may typically be a component of a detergent composition, e.g., a laundry detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The properties of the alpha-amylase of the invention make it particularly suitable for use in alkaline detergents, e.g. at pH 9.5–10.5, and for washing at low temperatures, e.g. 20–40° C.

The detergent composition of the invention may be in any convenient form, e.g. as powder, granules, paste or liquid. A liquid detergent may be aqueous, typically containing up to 70% water and 0–30% organic solvent, or non-aqueous. The detergent composition comprises one or more surfactants, each of which may be anionic, nonionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, cellulase, peroxidase, or oxidase, e.g., laccase.

Normally the detergent contains 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates. The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or encapsulated.

Examples of inorganic chlorine/bromine-type bleaches are lithium, sodium or calcium hypochlorite or hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

The oxygen-type bleach may be an inorganic persalt, preferably with a bleach activator, or a peroxy acid compound. Examples of inorganic persalts are alkali metal perborates, both tetrahydrates and monohydrates, alkali metal percarbonates, persilicates and perphosphates. The activator may be tetraacetylethylenediamine (TAED) or nonanoyloxybenzenesulfonate (NOBS).

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters, foam depressors, suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

More specifically, the alpha-amylase of the invention may be incorporated in any of the detergent formulations described in WO 96/23873.

The α-amylases of the invention may be incorporated in concentrations conventionally employed in detergents. It is at present contemplated that, in the detergent composition of the invention, the α-amylase may be added in an amount corresponding to 0.00001–1 mg (calculated as pure enzyme protein) of α-amylase per liter of wash liquor.

The present invention is further illustrated in the following examples which are not intended to be in any way limiting to the scope of the invention as claimed.

EXAMPLES

Host Organism:

Escherichia coli SJ2 is described in Diderichsen, B., Wedsted, U., Hedegaard, L., Jensen, B. R., Sjøholm, C. (1990) Journal of Bacteriology, Vol. 172, No. 8, p. 4315–4321.

Plasmids:

The gene bank vector was pSJ1678 which is further disclosed in WO94/19454 which is hereby incorporated by reference.

The gene bank vector pSJ1678 is further disclosed in WO 94/19454 which is hereby incorporated by reference.

Model Detergent:

A/P (Asia/Pacific) Model Detergent has the following composition: 20% STPP (sodium tripolyphosphate), 25% $Na_2SO_4$, 15% $Na_2CO_3$, 20% LAS (linear alkylbenzene sulfonate, Nansa 80S), 5% $C_{12}$–$C_{15}$ alcohol ethoxylate (Dobanol 25-7), 5% $Na_2Si_2O_5$, 0.3% NaCl.

Example 1

Cloning of alpha-amylase into E. coli

Figure 4:
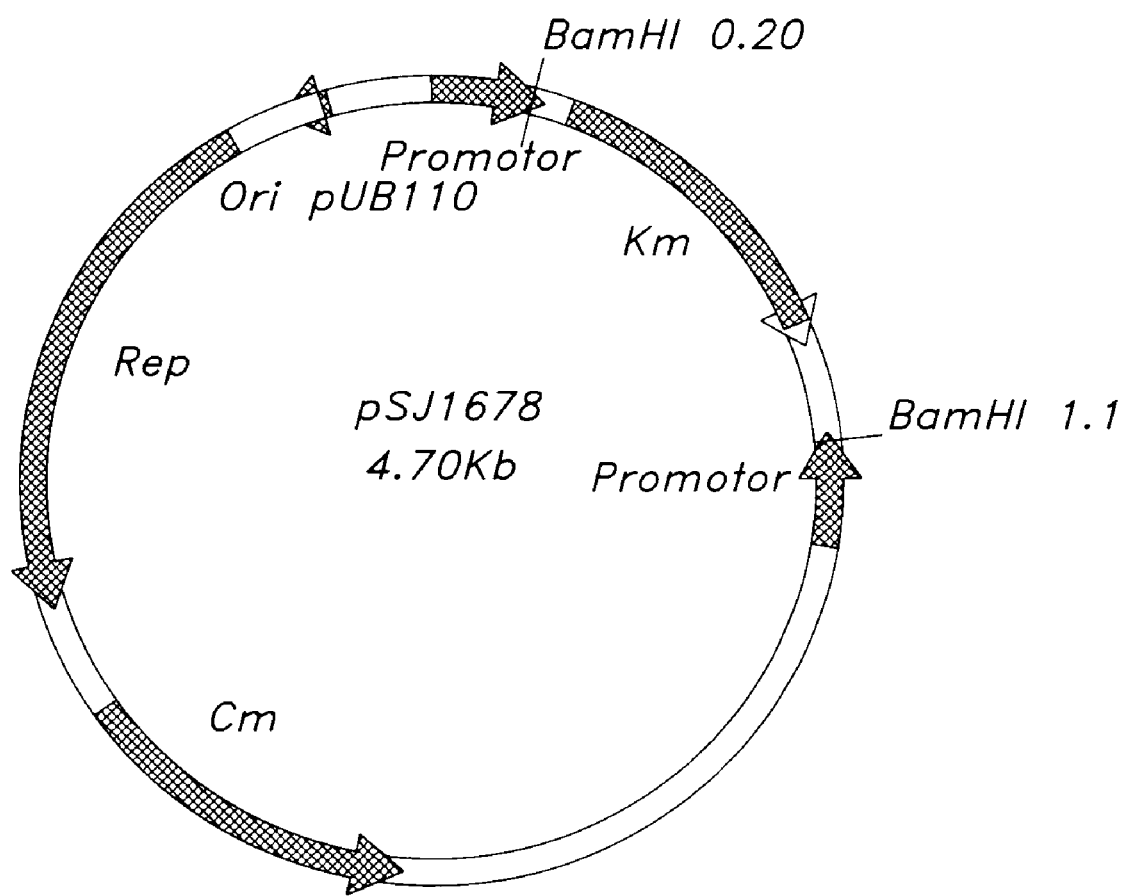
FIG. 4 shows the cloning vector pSJ1678 described in Example 1.

DNA was isolated from Bacillus sp. NCIMB 40916 by the method of Pitcher, D. G., Saunders, N. A., and Owen, R. J. (1989) Lett. Appl. Microbiol. 8, 151–156. Chromosomal DNA was partially digested with the restriction enzyme Sau3AI. The fragments were cloned into the BamHI site of the cloning vector pSJ1678, as shown in FIG. 4 and transformed into Escherichia coli SJ2, thereby creating a gene library of Bacillus sp. NCIMB 40916.

This gene library was screened for alpha amylase activity and the strain showing alpha amylase activity was termed Escherichia coli strain NN049489 comprises the full length alpha-amylase of the invention. This strain was deposited and given the accession number DSM 13001. Escherichia coli strain DSM 13001 (NN049489) harbouring the plasmid termed pJA386 encoding the full length alpha amylase was used for DNA sequencing. Further, Escherichia coli strain JA388 comprises a truncated alpha-amylase. This was deposited and given the accession number DSM 12662. Escherichia coli strain JA388 harbours the plasmid termed pJA388 encoding the truncated alpha amylase.

Example 2

Sequencing of DNA and alpha-amylase

The full length alpha amylase gene cloned in plasmid pJA386 was characterized by DNA sequencing by primer walking, using the Taq deoxyterminal cycle sequencing kit (Perkin Elmer, USA), fluorescent labeled terminators and appropriate oligonucleotides as primers.

Analysis of the sequence data was performed according to Devereux et al. (1984) Nucleic Acids Res. 12, 387–395. The sequence corresponds to the DNA sequence shown in SEQ ID NO: 3. The predicted protein sequence of the full length alpha amylase including the signal peptide and the mature alpha amylase are presented in SEQ ID NO: 4. The deduced N-terminal sequence was verified by sequencing 34 amino acids at the N-terminal of the protein.

Example 3

Production of alpha-amylase

E. coli DSm13001 (NN049489) harboring plasmid pJA386 was cultivated over night in LB-broth containing chloramphenicol 10 µg/ml, 37° C., 250 rpm. Cells were harvested from 2.7 l culture broth by centrifugation at 6000 rpm for 15 minutes. The intracellular located amylase was released from the cells by using the following osmotic shock procedure:

1) Cells were resuspended and washed in 500 ml 10 mM Tris-HCl, pH 7.0 (EKV-buffer) followed by centrifugation.

2) Cells were resuspended in 75 ml 20% sucrose, 30 mM Tris-HCl pH 8, 1 mM EDTA and added Lysozyme to a concentration of 5 mg/ml.

3) The solution was incubated 15 min on ice followed by centrifugation. The majority of the amylase was now contained in the supernatant.

The supernatant was dialyzed overnight against 10 l in EKV-buffer with one buffer change to decrease the high concentration of sucrose. The solution was filtered through a 0.45 μm membrane vacuum filter.

The enzyme solution was applied on a Pharmacia Q Sepharose column FF previously equilibrated in EKV-buffer, pH 7, and the column was washed with EKV-buffer. Bound proteins were eluted with a linear NaCl gradient from 0–500 mM over 10 column volumes. Amylase containing fractions were pooled and dialyzed against EKV-buffer over night.

The solution was then applied on a Q Sepharose column FF previously equilibrated in EKV-buffer, pH 8, the column was washed with EKV-buffer, and the amylase was eluted with a linear NaCl gradient from 0–500 mM over 10 column volumes. Amylase containing fractions were pooled.

A Phenyl Superose column previously equilibrated in EKV-buffer, pH 8 containing 1 M ammonium sulfate was loaded with the enzyme solution added ammonium sulfate to a concentration of 1 M. Unbound material was washed out with the ammonium sulfate buffer and the column was eluted with a linear NaCl gradient from 1–0 M ammonium sulfate over 20 column volumes. Amylase containing fractions were pooled.

The purified amylase was analyzed by SDS-PAGE and only one band was obtained after staining with Coomasie Blue.

Example 4

Washing Test of the Full Length alpha-amylase (SEQ ID NO: 4)

Washing performance was evaluated by washing soiled test swatches for 15 minutes at 25° C. in a detergent solution with the alpha-amylase of the invention.

The detergent used was the A/P Model Detergent described above at 3 g/l having pH 10.5, or a commercial detergent from Malaysia (FAB Total from Colgate) at 3 g/l having a pH of approx. 9.7. The purified amylase of Example 3 was added to the detergent solution at the concentration indicated below. The test swatches were soiled with orange rice starch (CS-28 swatches available from CFT, Center for Test Material, Holland).

After washing, the swatches were evaluated by measuring the remission at 460 nm. The results are expressed as ΔR=remission of the swatch washed with the alpha-amylase minus the remission of a swatch washed at the same conditions without the alpha-amylase.

| Alpha-amylase concentration (mg enzyme protein/l) | ΔR Model detergent | ΔR Malaysian detergent |
|---|---|---|
| 0 (reference) | = 0 | = 0 |
| 0.1 | 0.9 | 1 |
| 0.2 | 1.9 | 1.3 |
| 0.5 | 3 | 2.4 |
| 1.5 | 4.1 | 4.3 |

Figure 5:
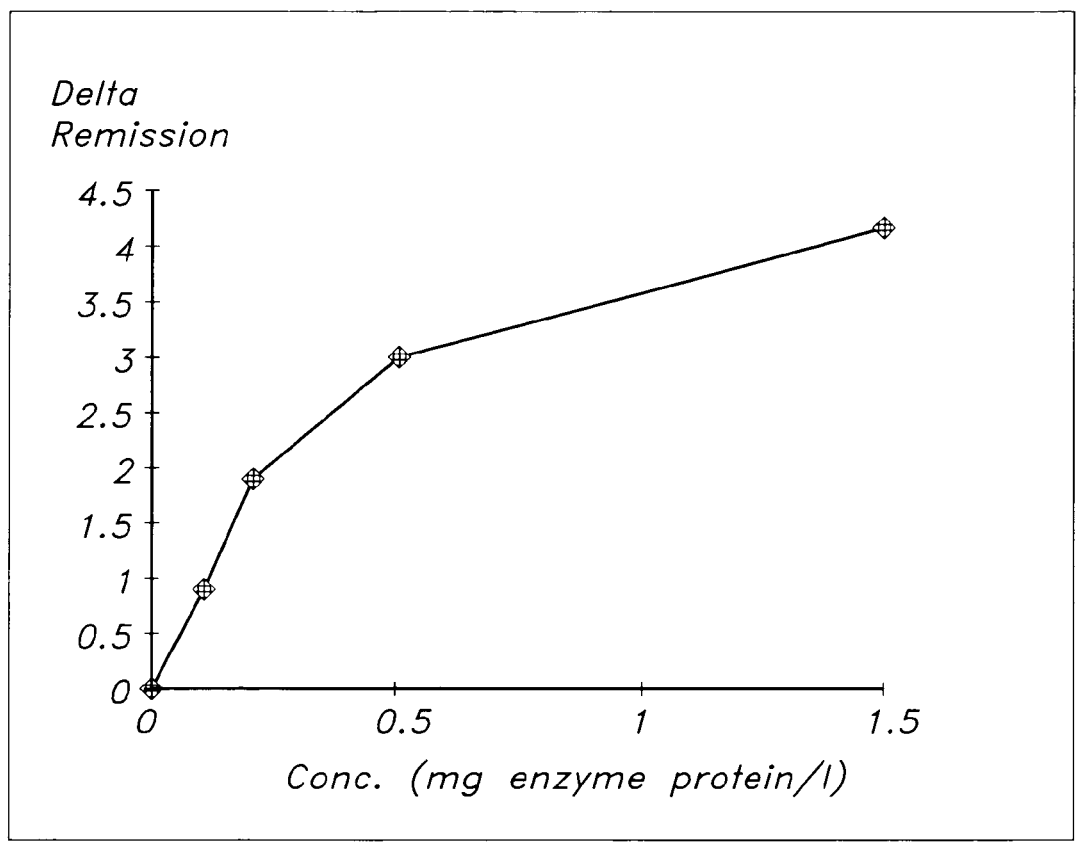
FIGS. 5 and 6 show results of washing tests described in Example 4.
Figure 6:
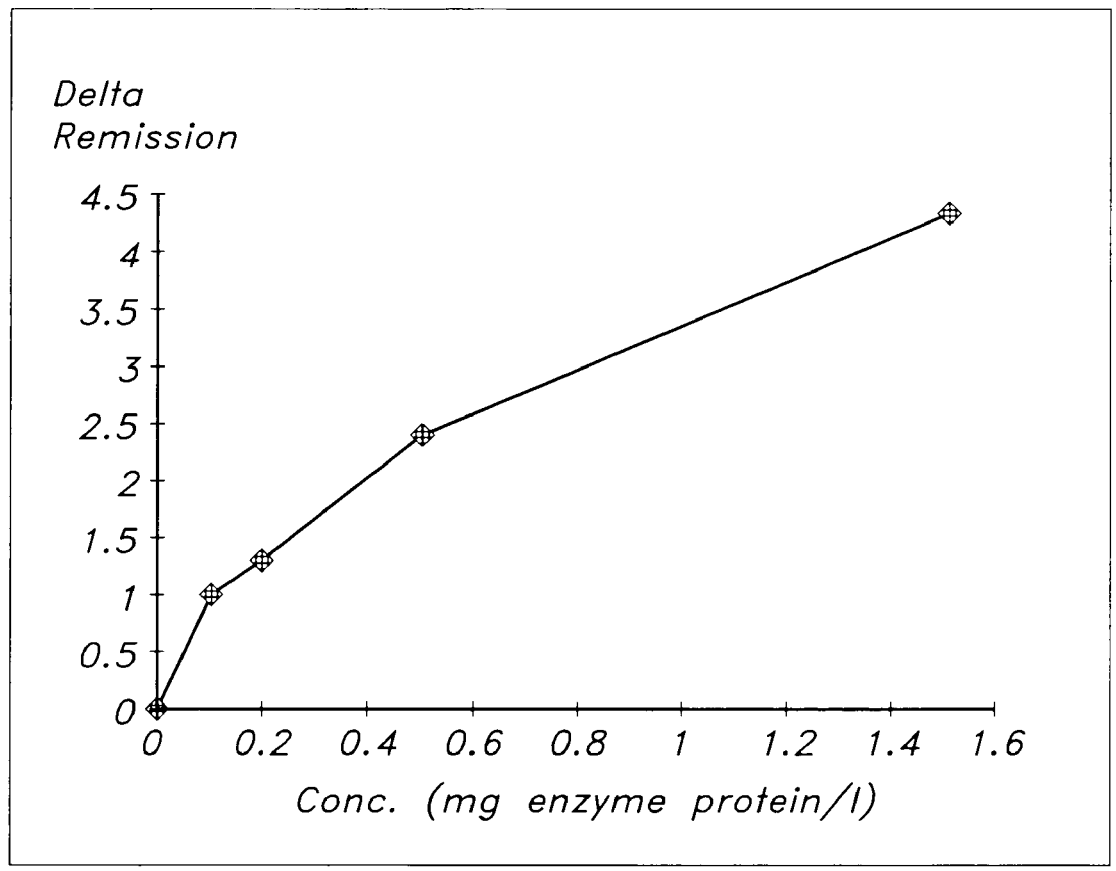

The results are shown in FIGS. 5 and 6. The results demonstrate that the alpha-amylase of the invention is effective in both detergents at highly alkaline pH.

What is claimed is:

1. An isolated alpha-amylase selected from the group consisting of:
   a) a polypeptide produced by *Bacillus* sp. NCIMB 40916,
   b) a polypeptide having an amino acid sequence as shown in positions 1–556 of SEQ ID NO: 4,
   c) a polypeptide encoded by the alpha-amylase encoding part of the DNA sequence cloned into a plasmid present in *Escherichia coli* DSM 13001 (NN049489), and
   d) a polypeptide that:
      i) is at least 60% homologous with the polypeptide defined in (a) or (b), or
      ii) is derived from the polypeptide defined in (a) or (b) by one or more of substitution, deletion or insertion of one or more amino acids.

2. An isolated alpha-amylase having an enzymatic activity at pH 10.5 that is at least two times higher than the activity at pH 7.3 when measured at 37° C.

3. An isolated alpha-amylase having an enzymatic activity at pH 9.5 that is at least 4 times higher than the activity at pH 7.3 when measured at 37° C.

4. The alpha-amylase of claim 1, wherein said alpha-amylase is derived from a strain of *Bacillus*.

5. The alpha-amylase of claim 1, wherein said alpha-amylase retains more than 90% of its activity after 20 minutes incubation at 25° C. in a solution of 3 g/l of a test detergent containing 20% sodium tripolyphosphate (STPP), 25% $Na_2SO_4$, 15% $Na_2CO_3$, 20% linear alkylbenzene sulfonate (LAS), 5% $C_{12}$–$C_{15}$ alcohol ethoxylate, 5% $Na_2Si_2O_5$, 0.3% NaCl at pH 10.5 and 6 degrees German hardness, and retains less than 90% of its activity after 20 minutes incubation at 30° C. in the same solution.

6. The alpha-amylase of claim 1 which has a molecular weight of about 55 kDa as determined by SDS-PAGE.

7. The alpha-amylase of claim 1 which has an iso-electric point of about 5 as determined by isoelectric focusing.

8. The alpha-amylase of claim 1 in the form of a detergent additive which is a non-dusting granulate or a stabilized liquid.

9. A method for producing the alpha-amylase of claim 1, comprising cultivating an amylase-producing strain of *Bacillus* in a suitable nutrient medium, and recovering the alpha-amylase from the culture medium.

10. A detergent composition comprising the alpha-amylase of claim 1 and a surfactant.

11. The detergent composition of claim 10, wherein said composition has a pH of 8.5–11 in aqueous solution.

12. The detergent composition of claim 11 which is a laundry detergent.

* * * * *